United States Patent
Liu et al.

(10) Patent No.: US 12,378,881 B2
(45) Date of Patent: Aug. 5, 2025

(54) METHOD FOR DETERMINING ROCK MATRIX AND FRACTURE PERMEABILITY BY USING POROELASTODYNAMICS AND DENSITY AVERAGING SCHEMES

(71) Applicant: ARAMCO SERVICES COMPANY, Houston, TX (US)

(72) Inventors: Chao Liu, Brookshire, TX (US);
Vladimir Kazei, Houston, TX (US);
Dung T. Phan, Brookshire, TX (US);
Younane N. Abousleiman, Norman, OK (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 550 days.

(21) Appl. No.: 17/804,273

(22) Filed: May 26, 2022

(65) Prior Publication Data
US 2023/0383648 A1 Nov. 30, 2023

(51) Int. Cl.
*E21B 49/08* (2006.01)
*E21B 49/00* (2006.01)
(Continued)

(52) U.S. Cl.
CPC .......... *E21B 49/088* (2013.01); *E21B 49/005* (2013.01); *G01N 33/241* (2013.01); *G01V 1/306* (2013.01); *E21B 2200/20* (2020.05)

(58) Field of Classification Search
CPC .. E21B 49/088; E21B 49/005; E21B 2200/20; G01N 33/241; G01V 1/306; G01V 1/50
See application file for complete search history.

(56) References Cited

U.S. PATENT DOCUMENTS

| 8,184,502 B2 | 5/2012 | Xu et al. |
| 8,649,980 B2 | 2/2014 | Gulati |

(Continued)

FOREIGN PATENT DOCUMENTS

CN 112485827 A 3/2021

OTHER PUBLICATIONS

Wen et al., Poroelastodynamic solution for an incline borehole subjected to non-hydrostatic, 2018, American Rock Mechanics Association, ARMA 18-274, pp. 1-11 (Year: 2018).*

(Continued)

*Primary Examiner* — Mi'schita' Henson
(74) *Attorney, Agent, or Firm* — Osha Bergman Watanabe & Burton LLP

(57) ABSTRACT

A method of determining rock matrix and fracture permeability to perform a reservoir fluid flow simulation. The method includes: obtaining a petrophysical characterization of a formation sample, measuring a first and second elastic wave velocity of the formation sample at a first and second frequency, calculating an average rock matrix density and an average porosity of the formation sample, determining a set of calculated elastic wave velocities for the first and second frequencies over a range of candidate permeabilities, and determining a rock matrix permeability and a fracture permeability based on the set of calculated elastic wave velocities at the first and second frequency respectively. The method further including performing a reservoir fluid flow simulation based, at least in part, on at least one of the rock matrix permeability and the fracture permeability.

12 Claims, 8 Drawing Sheets

(51) Int. Cl.
  *G01N 33/24* (2006.01)
  *G01V 1/30* (2006.01)

(56) References Cited

U.S. PATENT DOCUMENTS

| | | | |
|---|---|---|---|
| 9,835,609 | B2 | 12/2017 | Liu et al. |
| 11,111,784 | B2 | 9/2021 | Willberg et al. |
| 11,519,879 | B2 * | 12/2022 | Liu .................. G01N 33/241 |

OTHER PUBLICATIONS

Liu et al., Determination of the Connected and Isolated Porosities by a Poroelastodynamics Model, 2024, pp. 1-12, International Petroleum Technology Conference, IPTC-23741-EA, DOI 10.2523/IPTC-23741-EA (Year: 2024).*

Liu et al. Anisotropic Poroelastodynamics Solution and Elastic Moduli Dispersion of a Naturally Fractured Rock, 2023, Society of Petroleum Engineers, SPE-213366-MS, pp. 1-8, DOI 10.2118/213366-MS (Year: 2023).*

Temizel et al., "A Review of Hydraulic Fracturing and Latest Developments in Unconventional Reservoirs", May 2-5, 2022, OTC-31942-MS, Offshore Technology Conference DOI 10.4043/31942-MS, pp. 1-70 (Year: 2022)*

Liu, Chao, "Dual-Porosity Dual-Permeability Poroelastodynamics Analytical Solutions for Mandel's Problem"; Journal of Applied Mechanics; vol. 88, Issue 1, Article 011002; pp. 011002-1-011002-10; Jan. 2021 (10 pages).

Liu, Chao et al., "Poroelastic Dual-Porosity/Dual-Permeability After-Closure Pressure-Curves Analysis in Hydraulic Fracturing"; SPE Journal; vol. 22, Issue 1, Paper No. SPE-181748-PA; pp. 198-218; Feb. 2017 (21 pages).

Mehrabian, Amin et al., "Mandel's problem reloaded"; Journal of Sound and Vibration; vol. 492, Article 115785; pp. 1-16; Feb. 3, 2021 (16 pages).

Pride, Steven R et al., "Linear dynamics of double-porosity dual-permeability materials. I. Governing equations and acoustic attenuation"; Physical Review E; vol. 68, Issue 3, Article 036603; pp. 036603-1-036603-10; Sep. 9, 2003 (10 pages).

* cited by examiner

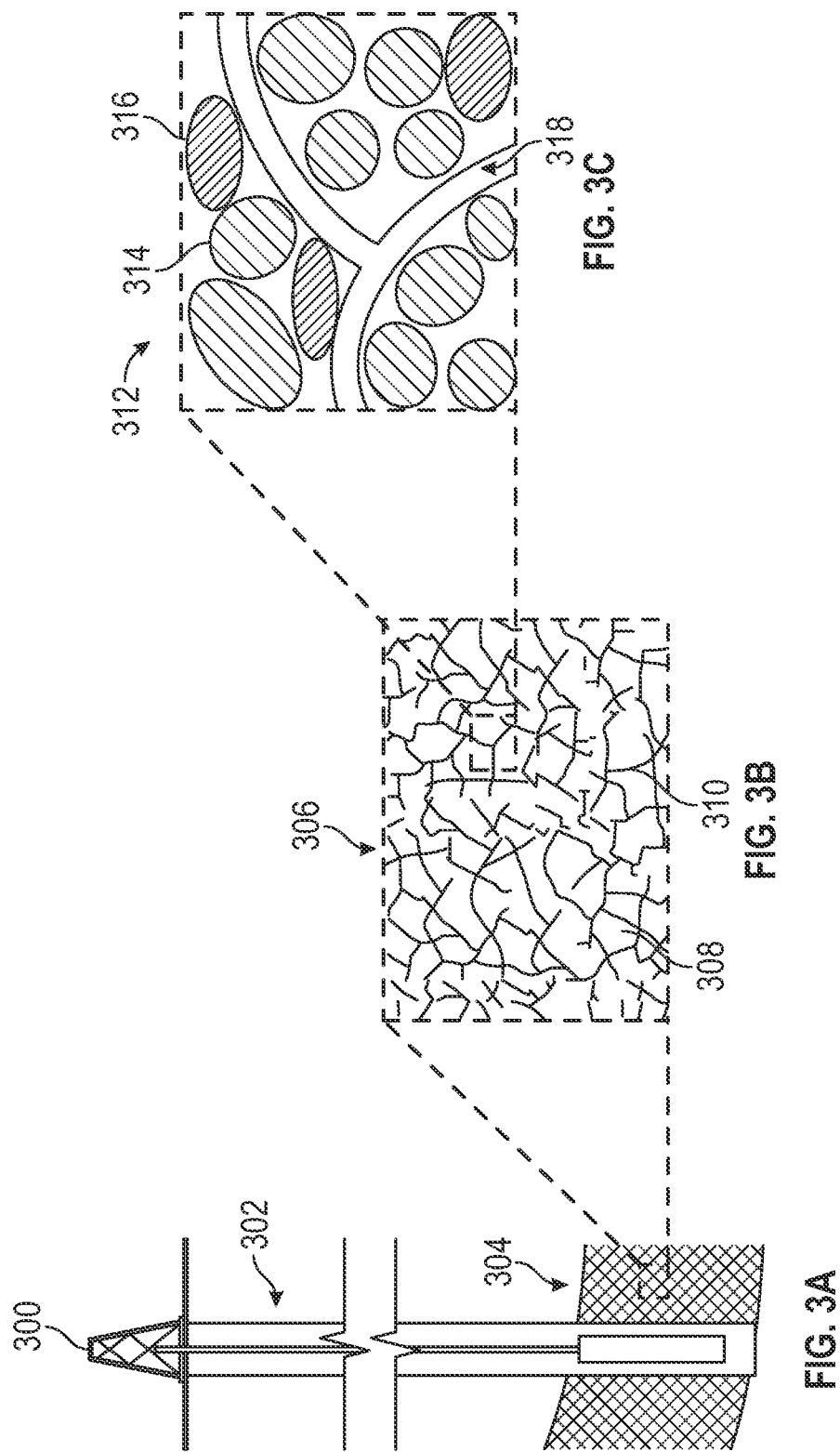

| Parameters | Rock Matrix (1) | Fractures (2) |
| --- | --- | --- |
| Bulk Modulus, K (GPa) | 8.4 | 0.21 |
| Poisson's Ratio, $\nu$ | 0.181 | 0.181 |
| Biot's Coefficient, $\alpha$ | 0.729 | 1.0 |
| Skempton's Coefficient, B | 0.498 | 0.9 |
| Volume Fraction, v (%) | 98.2 | 1.8 |
| Porosity, $\phi$ | 0.191 | 1.0 |
| Tortuosity, $\tau$ | 3.1 | 1.0 |

FIG. 5

METHOD FOR DETERMINING ROCK MATRIX AND FRACTURE PERMEABILITY BY USING POROELASTODYNAMICS AND DENSITY AVERAGING SCHEMES

BACKGROUND

Permeability is a key parameter in many industries and applications. Permeability measures the ease with which fluid flows through a porous solid material, such as a rock. In a higher permeability material fluid may flow more easily through the solid material than in a lower permeability material. In the oil and gas industry permeability estimates are used in a wide range of applications such as, estimating production and injection rates, estimating reservoir volumes and recoverable reserves, planning production facilities, planning well drilling programs, and designing enhanced recovery programs. It is therefore desirable to have a method to accurately estimate permeability.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments disclosed herein relate to a method of determining rock matrix permeability and fracture permeability to perform a reservoir fluid flow simulation. The method includes: obtaining a petrophysical characterization of a formation sample, measuring a first elastic wave velocity of the formation sample at a first frequency and measuring a second elastic wave velocity of the formation sample at a second frequency. Having the petrophysical characterization and measurements, the method further includes: calculating an average rock matrix density and an average porosity of the formation sample, determining a set of calculated elastic wave velocities for the first frequency over a range of candidate permeabilities and a set of calculated elastic wave velocities for the second frequency over the range of candidate permeabilities, determining a rock matrix permeability based, at least in part, on the set of calculated elastic wave velocities at the first frequency for the average rock matrix density and the average porosity, determining a fracture permeability based, at least in part, on the set of calculated elastic wave velocities at the second frequency for the average rock matrix density and the average porosity. The method still further including performing a reservoir fluid flow simulation based, at least in part, on at least one of the rock matrix permeability and the fracture permeability.

In general, in one aspect, embodiments disclosed herein relate to a system to perform a reservoir fluid flow simulation and determine a wellbore path. The system includes: a core sample analyzer configured to determine a petrophysical characterization of a formation sample, and measure an elastic wave velocity at a first frequency and a second frequency for the formation sample. The system further including a computer processor configured to receive the petrophysical characterization of the formation sample, receive the first measured elastic wave velocity of the formation sample at a first frequency and the second measured elastic wave velocity of the formation sample at a second frequency, calculate, based at least in part, on the petrophysical characterization, an average rock matrix density and an average porosity of the formation sample, determine a set of calculated elastic wave velocities for the first frequency over a range of candidate permeabilities and a set of calculated elastic wave velocities for the second frequency over the range of candidate permeabilities, determine a rock matrix permeability based, at least in part, on the set of calculated elastic wave velocities at the first frequency for the average rock matrix density and the average porosity, and determine a fracture permeability based, at least in part, on the set of calculated elastic wave velocities at the second frequency for the average rock matrix density and the average porosity, The computer processor of the system further configured to perform a reservoir fluid flow simulation based, at least in part, on at least one of the rock matrix permeability and the fracture permeability, and determine a wellbore path based, at least in part, on the reservoir fluid flow simulation.

In general, in one aspect, embodiments disclosed herein relate to a non-transitory computer readable medium storing a set of instructions executable by a computer processor, the set of instructions including the functionality for: receiving a petrophysical characterization of a formation sample, receiving a first measured elastic wave velocity of the formation sample at a first frequency and a second measured elastic wave velocity of the formation sample at a second frequency, wherein the first frequency is lower than the second frequency, calculating, based at least in part, on the petrophysical characterization, an average rock matrix density and an average porosity of the formation sample, determining a set of calculated elastic wave velocities for the first frequency over a range of candidate permeabilities and a set of calculated elastic wave velocities for the second frequency over the range of candidate permeabilities, determining a rock matrix permeability based, at least in part, on the set of calculated elastic wave velocities at the first frequency for the average rock matrix density and the average porosity, and determining a fracture permeability based, at least in part, on the set of calculated elastic wave velocities at the second frequency for the average rock matrix density and the average porosity. The instruction further including the functionality for performing a reservoir fluid flow simulation based, at least in part, on at least one of the rock matrix permeability and the fracture permeability.

Other aspects and advantages of the claimed subject matter will be apparent from the following description and the appended claims.

BRIEF DESCRIPTION OF DRAWINGS

FIG. 3a shows a drilling system and wellbore intersecting a subsurface formation in accordance with one or more embodiments.

FIG. 3b depicts a magnified sample of the subsurface formation indicating that the subsurface formation may be a fractured formation in accordance with one or more embodiments.

FIG. 3c depicts a further magnified sample of the fracture formation having a dual-porosity and dual-permeability in accordance with one or more embodiments.

FIG. 5 provides an example petrophysical characterization table in accordance with one or more embodiments.

DETAILED DESCRIPTION

Figure 1:
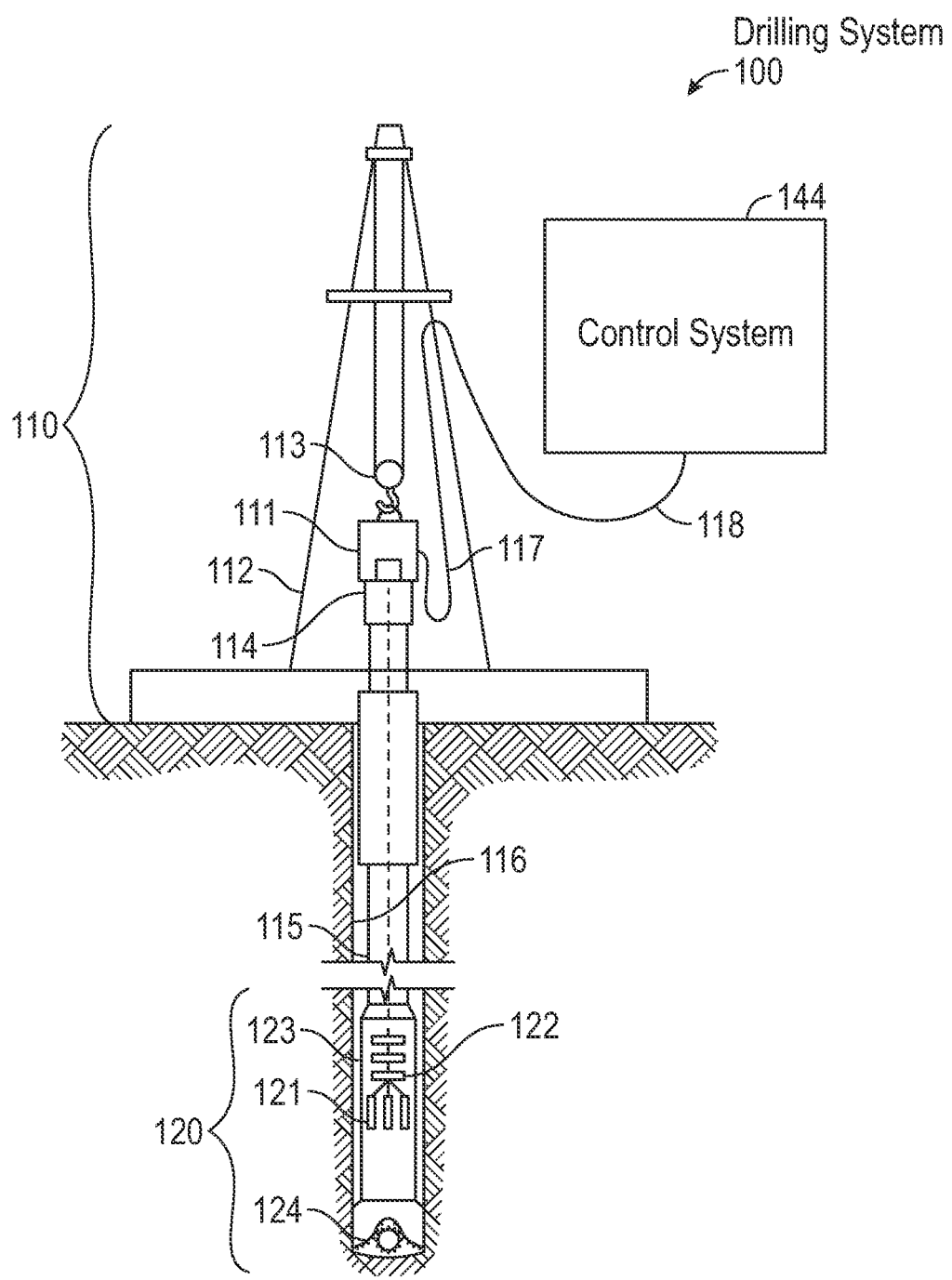
FIG. 1 illustrates a drilling system in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-9, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a formation sample" includes reference to one or more of such samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Permeability is a measure of the ease with which a fluid flows through a solid porous material and is a key parameter in many industries and applications. In the oil and gas industry permeability estimates are used in a wide range of applications such as, estimating production and injection rates, estimating reservoir volumes and recoverable reserves, planning production facilities, planning well drilling programs, and designing enhanced recovery programs. It is therefore desirable to have a method to accurately estimate permeability. The method described herein uses a dual porosity dual permeability poroelastodynamic model to determine estimates for a rock matrix permeability and a fracture permeability. In some implementation of the method at least one of the rock matrix permeability and fracture permeability are directed to performing a fluid flow simulation to facilitate the design of a wellbore path for a drilling system. In other implementations the fluid flow simulation may be used to determine other useful information that directs economic and drilling decisions such as a production rate, an injection rate, a recoverable reserves volume or when planning a production facility, a well drilling program, or an enhanced recovery program.

FIG. 1 illustrates a drilling system in accordance with one or more embodiments. As shown in FIG. 1, a drilling system (100) may include a top drive drill rig (110) arranged around the setup of a drill bit logging tool (120). A top drive drill rig (110) may include a top drive (111) that may be suspended in a derrick (112) by a travelling block (113). In the center of the top drive (111), a drive shaft (114) may be coupled to a top pipe of a drill string (115), for example, by threads. The top drive (111) may rotate the drive shaft (114), so that the drill string (115) and a drill bit logging tool (120) cut the rock at the bottom of a wellbore (116). A power cable (117) supplying electric power to the top drive (111) may be protected inside one or more service loops (118) coupled to a control system (144). As such, drilling mud may be pumped into the wellbore (116) through a mud line, the drive shaft (114), and/or the drill string (115).

Moreover, when completing a well, casing may be inserted into the wellbore (116). The sides of the wellbore (116) may require support, and thus the casing may be used for supporting the sides of the wellbore (116). As such, a space between the casing and the untreated sides of the wellbore (116) may be cemented to hold the casing in place. The cement may be forced through a lower end of the casing and into an annulus between the casing and a wall of the wellbore (116). More specifically, a cementing plug may be used for pushing the cement from the casing. For example, the cementing plug may be a rubber plug used to separate cement slurry from other fluids, reducing contamination and maintaining predictable slurry performance. A displacement fluid, such as water, or an appropriately weighted drilling mud, may be pumped into the casing above the cementing plug. This displacement fluid may be pressurized fluid that serves to urge the cementing plug downward through the casing to extrude the cement from the casing outlet and back up into the annulus.

As further shown in FIG. 1, sensors (121) may be included in a sensor assembly (123), which is positioned adjacent to a drill bit (124) and coupled to the drill string (115). Sensors (121) may also be coupled to a processor assembly (123) that includes a processor, memory, and an analog-to-digital converter (122) for processing sensor measurements. For example, the sensors (121) may include acoustic sensors, such as accelerometers, measurement microphones, contact microphones, and hydrophones. Likewise, the sensors (121) may include other types of sensors, such as transmitters and receivers to measure resistivity, gamma ray detectors, etc. The sensors (121) may include hardware and/or software for generating different types of well logs (such as acoustic logs or density logs) that may provide well data about a wellbore, including porosity of wellbore sections, gas saturation, bed boundaries in a geologic formation, fractures in the wellbore or completion cement, and many other pieces of information about a formation. If such well data is acquired during drilling operations (i.e., logging-while-drilling), then the information may be used to make adjustments to drilling operations in real-time. Such adjustments may include rate of penetration (ROP), drilling direction, altering mud weight, and many others drilling parameters.

In some embodiments, acoustic sensors may be installed in a drilling fluid circulation system of a drilling system (100) to record acoustic drilling signals in real-time. Drilling acoustic signals may transmit through the drilling fluid to be recorded by the acoustic sensors located in the drilling fluid circulation system. The recorded drilling acoustic signals may be processed and analyzed to determine well data, such as lithological and petrophysical properties of the rock formation. This well data may be used in various applications, such as steering a drill bit using geosteering, casing shoe positioning, etc.

The control system (144) may be coupled to the sensor assembly (123) in order to perform various program functions for up-down steering and left-right steering of the drill bit (124) through the wellbore (116). More specifically, the control system (144) may include hardware and/or software with functionality for geosteering a drill bit through a formation in a lateral well using sensor signals, such as drilling acoustic signals or resistivity measurements. For example, the formation may be a reservoir region, such as a pay zone, bed rock, or cap rock.

While FIG. 1 shows a possible configuration of components, other configurations may be used without departing from the scope of the disclosure. For example, various components in FIG. 1 may be combined to create a single component. As another example, the functionality performed by a single component may be performed by two or more components.

Figure 2A:
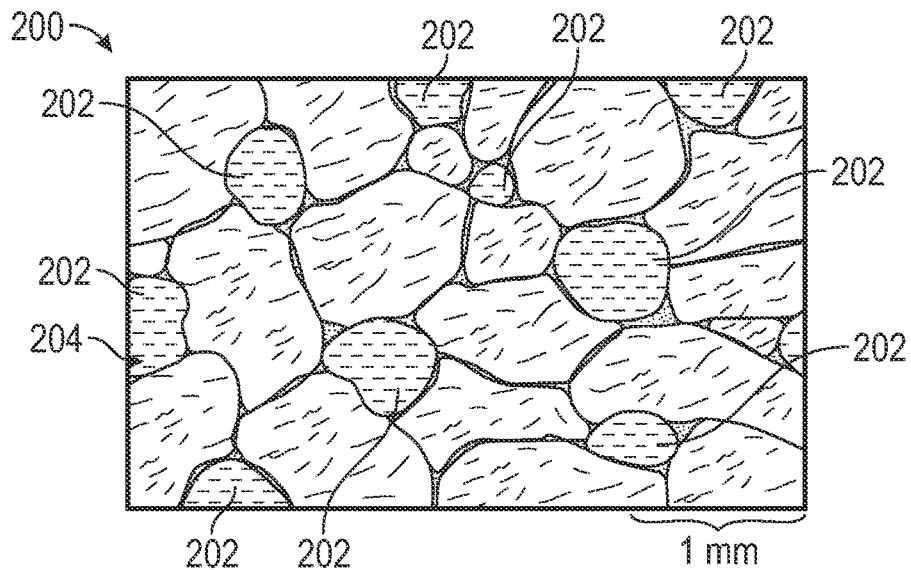
FIG. 2a illustrates a 2D cross-section of a porous medium with isolated pore spaces.
Figure 2B:
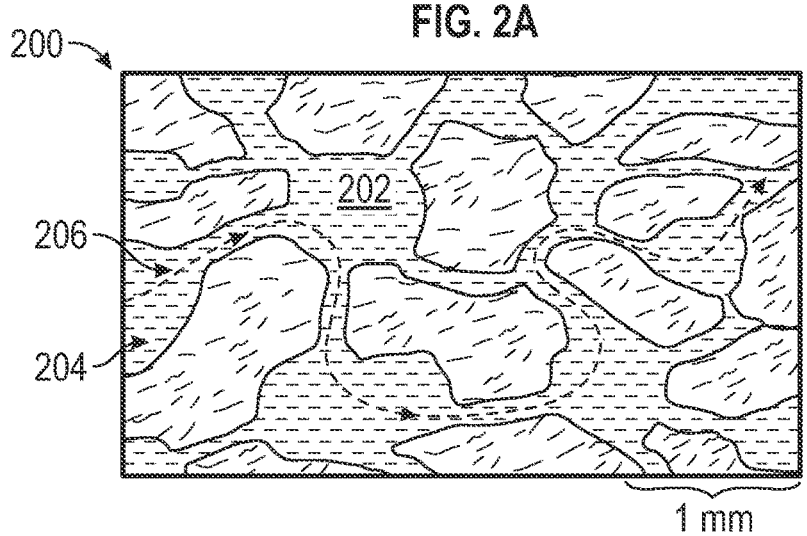
FIG. 2b illustrates a 2D cross-section of a porous medium with interconnected pore spaces.
Figure 2C:
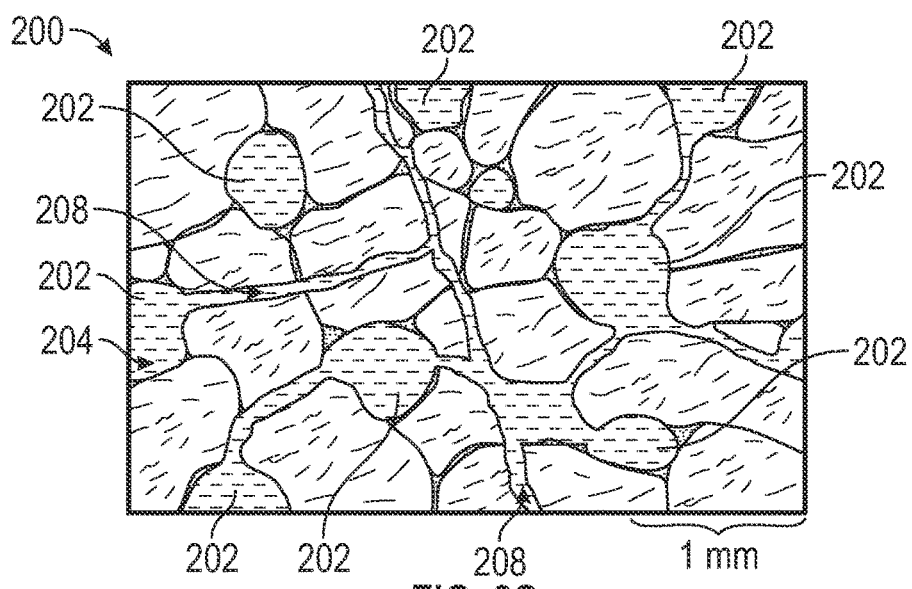
FIG. 2c illustrates a 2D cross-section of a porous medium with a plurality of fractures.

FIG. 2a illustrates a 2D cross-section of porous medium (200) that has a plurality of pore spaces (202). Pore spaces are voids within a porous material that may be filled with gas or liquid or a combination of both. Porosity describes the volume of pore space (202) divided by the total volume of the material and may be expressed as a percentage. The pore spaces (202) may be filled with a fluid (204) such as gas, water, and hydrocarbons. If the pore spaces (202) are not connected, i.e., there is no pathway for the fluids (204) contained in each pore space (202) to move between the pore spaces (202) and the fluid (204) will not be able to flow through the porous media (200). FIG. 2b illustrates a 2D cross-section of a porous medium (200) in which the pore spaces (202) are interconnected as depicted by a potential fluid pathway (206). If the pore spaces (202) interconnect the fluid (204) may be able to flow. Permeability describes the ability of a fluid (204) to flow through the pore spaces (202) of the porous medium (200). FIG. 1c illustrates a 2D cross-section of a porous medium that may include a plurality of fractures (208). The fractures (208) may also be filled with a fluid (204). In some case the fractures (208) may add to the pore space (202) of the porous material (200) and may increase the interconnection between pore spaces. In other cases the fractures (208) may be filled material, e.g., precipitants from the fluid, that may reduce the pore space and interconnected fluid pathways (206).

FIG. 3a shows a drilling system (300) and wellbore (302) intersecting a subsurface formation (304), which may be a reservoir formation, and the reservoir formation may be a fractured formation in accordance with one or more embodiments. FIG. 3b illustrates a magnification of a fractured formation sample (306) comprising a rock matrix component (308) and a fracture component (310). FIG. 3c illustrates a further magnification of the fractured formation sample (312) where the rock matrix may include of a mineral grain component (314) with a mineral grain density and a mineral grain volume fraction, an organic material component (316) with an organic material density and an organic material volume fraction, and a fracture (318) with a volume fraction of the fracture. The fractured formation sample also includes pore spaces in both the rock matrix and the fracture which contribute to a total porosity. The fractured formation sample may simulate a dual-porosity dual-permeability porous medium. The interaction of an elastic wave with the porous medium may be described by poroelastodynamics.

The dual-porosity dual-permeability poroelastodynamic model is formulated in a solid-fluid displacement form of $u_i$-$w_i$ as follows.

$$(\lambda + G - \overline{\alpha}_1 a_{11} - \overline{\alpha}_2 a_{21})\nabla(\nabla \cdot u) + \qquad \text{Equation (1)}$$
$$G\nabla^2 u - (\overline{\alpha}_1 a_{12} + \overline{\alpha}_2 a_{22})\nabla(\nabla \cdot w_1) -$$
$$(\overline{\alpha}_1 a_{13} + \overline{\alpha}_2 a_{23})\nabla(\nabla \cdot w_2) + \omega^2 \rho u + \omega^2 \rho_f w_1 + \omega^2 \rho_f w_2 = 0$$

$$a_{11}\nabla(\nabla \cdot u) + a_{12}\nabla(\nabla \cdot w_1) + a_{13}\nabla(\nabla \cdot w_2) = \qquad \text{Equation (2)}$$
$$\omega^2 \rho_f u + \left(\omega^2 \frac{\tau_1 \rho_f}{v_1 \phi_1} + \frac{i\omega}{\kappa_{11}}\right) w_1 + \omega^2 \frac{\rho_{23}}{v_1 v_2 \phi_1 \phi_2} w_2$$

$$a_{21}\nabla(\nabla \cdot u) + a_{22}\nabla(\nabla \cdot w_1) + a_{23}\nabla(\nabla \cdot w_2) = \qquad \text{Equation (3)}$$
$$\omega^2 \rho_f u + \omega^2 \frac{\rho_{23}}{v_1 v_2 \phi_1 \phi_2} w_1 + \left(\omega^2 \frac{\tau_2 \rho_f}{v_2 \phi_2} + \frac{i\omega}{\kappa_{22}}\right) w_2$$

where u may be a displacement vector of a solid, $w_j$ may be a relative displacement of fluid in a porous medium j with respect to the solid, λ and G may be Lamé parameters, i may be an imaginary unit, $\overline{\alpha}_j$ may be an effective Biot's coefficient, ω may be an angular frequency, $\tau_j$ and $\phi_j$ may be a tortuosity and a porosity of the porous medium j, $\kappa_{11}$ and $\kappa_{22}$ may the mobilities of the dual-porosity media, $v_j$ may be a volume fraction of the rock matrix or fracture of the porous medium, $a_{mm}$ may be stiffness coefficients, ρ is the total bulk density, and $\rho_f$ is the pore fluid density. In general, a parameter used may be replaced or substituted with another parameter through known equivalents or conversions that would be known to a person of skill in the art.

Based on equations (1)-(3), the elastic wave velocity for a shear wave (S-wave), $V_s$, or compressional wave (P-wave), $V_{p1}$, $V_{p2}$, and $V_{p3}$, may be calculated.

The shear wave velocity (Vs) may be given by:

$$V_s = \sqrt{\frac{G}{\rho + \frac{2b_{12} - b_{11} - b_{22}}{b_{11}b_{22} - b_{12}^2}\rho_f^2}} \quad \text{Equation (4)}$$

where, $b_{11} = \frac{\tau_1 \rho_f}{v_1 \phi_1} + \frac{i}{\omega \kappa_{11}}$  Equation (5a)

$b_{12} = \frac{\rho_{23}}{v_1 v_2 \phi_1 \phi_2}$,  Equation (5b)

$b_{22} = \frac{\tau_2 \rho_f}{v_2 \phi_2} + \frac{i}{\omega \kappa_{22}}$  Equation (5c)

The compressional wave velocities ($V_{p1}$, $V_{p2}$, and $V_{p3}$) may be given by:

$$V_{p1} = \frac{\omega}{\sqrt{-\lambda_1}} \quad \text{Equation (6a)}$$

$$V_{p2} = \frac{\omega}{\sqrt{-\lambda_2}} \quad \text{Equation (6b)}$$

$$V_{p3} = \frac{\omega}{\sqrt{-\lambda_3}} \quad \text{Equation (6c)}$$

where $V_{p1}$ is a velocity of the fastest compressional wave, $V_{p2}$ and $V_{p3}$ are velocities of a second and a third P-wave, and $\lambda_1$, $\lambda_2$, and $\lambda_3$ may be the eigenvalues of the following matrix $$P = \omega^2 \begin{bmatrix} n_{11} & n_{12} & n_{13} \\ a_{11} & a_{12} & a_{13} \\ a_{21} & a_{22} & a_{23} \end{bmatrix}^{-1} \begin{bmatrix} -\rho & -\rho_f & -\rho_f \\ \rho_f & b_{11} & b_{12} \\ \rho_f & b_{12} & b_{22} \end{bmatrix} \quad \text{Equation (7)}$$

$n_{11} = \lambda + 2G - \overline{\alpha}_1 a_{11} - \overline{\alpha}_2 a_{21}$  Equation (8a)

$n_{12} = -(\overline{\alpha}_1 a_{12} + \overline{\alpha}_2 a_{22})$  Equation (8b)

$n_{13} = -(\overline{\alpha}_1 a_{13} + \overline{\alpha}_2 a_{23})$  Equation (8c)

For the dual-porosity dual-permeability medium, a rock matrix density of the fractured formation sample may be an average value of the mineral grain density and the organic material density. The rock matrix density may be highly impacted by the quantity and distribution of the mineral grains and the organic material present. Therefore, an average rock matrix density is dependent on how well the average scheme represents the rock matrix component.

The average value of the rock matrix density and the overall porosity may be calculated in a variety of ways which in some implementations of the method may be an arithmetic average, a geometric average, and a harmonic average. In the formulation of the model: the arithmetic average for the rock matrix density ($\rho_A$) and the total porosity ($\phi_A$) may be given by, $$\rho_A = \frac{v_{11}}{v_1}\rho_1 + \frac{v_{12}}{v_1}\rho_2 + \cdots + \frac{v_{1N}}{v_1}\rho_N \quad \text{Equation (9a)}$$

$$\phi_A = v_1\phi_1 + v_2\phi_2 \quad \text{Equation (9b)}$$

the geometric average of the rock matrix density ($\rho_G$) and total porosity ($\phi_G$) may be given by, $$\rho_G = \sqrt[v_1]{\rho_1}^{v_{11}} \sqrt[v_1]{\rho_2}^{v_{12}} \cdots \sqrt[v_1]{\rho_N}^{v_{1N}} \quad \text{Equation (10a)}$$

$$\phi_G = \sqrt[v_1]{\phi_1} \sqrt[v_2]{\phi_2} \quad \text{Equation (10b)}$$

and the harmonic average of the rock matrix density ($\rho_H$) and the total porosity ($\phi_H$) may be given by, $$\rho_H = \frac{1}{\frac{v_{11}/v_1}{\rho_1} + \frac{v_{12}/v_1}{\rho_2} + \cdots + \frac{v_{1N}/v_1}{\rho_N}} \quad \text{Equation (11a)}$$

$$\phi_H = \frac{1}{\frac{v_1}{\phi_1} + \frac{v_2}{\phi_2}} \quad \text{Equation (11b)}$$

where $v_{11}, v_{12}, \ldots, v_{1N}$ are the volume fractions of the mineral grain components and the organic material components and $v_{11} + v_{12} + \ldots + v_{1N} = v_1$.

In other embodiments the average may include other types of averaging schemes such as weighted variations of the arithmetic average, geometric average, or harmonic average.

An elastic wave phase velocity spectrum may be calculated in terms of rock matrix permeability ($k_1$), $k_1 = \kappa_{11}\mu$, and fracture permeability ($k_2$), $k_2 = \kappa_{22}\mu$, where $\mu$ is the pore fluid viscosity, such that the at a specific frequency, a set of calculated elastic wave velocities over a range of candidate permeabilities can be determined. The function may be plotted graphically or written to computer memory by a computer processor.

A measured elastic wave velocity may be measured in the field or laboratory or may be derived from other available data. In materials where elastic wave velocity varies as a function of wave frequency two distinct velocities may be defined. A phase velocity describes the rate at which crests of the wave move through the material and a group velocity describes the rate at which a packet of waves, and the energy carried by the packet, moves through the material. In accordance with one or more embodiments, the measured elastic wave velocity may be a measured elastic wave phase velocity. The elastic wave phase velocity is the elastic wave velocity of a single frequency component of the elastic wave. For example, a compressional wave (P-wave) velocity at a given frequency, e.g., 1 Hz, 10 Hz, 100 Hz, 1 kHz, 10 kHz. The measured elastic wave phase velocity may be displayed graphically and/or written to computer memory for later use.

Figure 4:
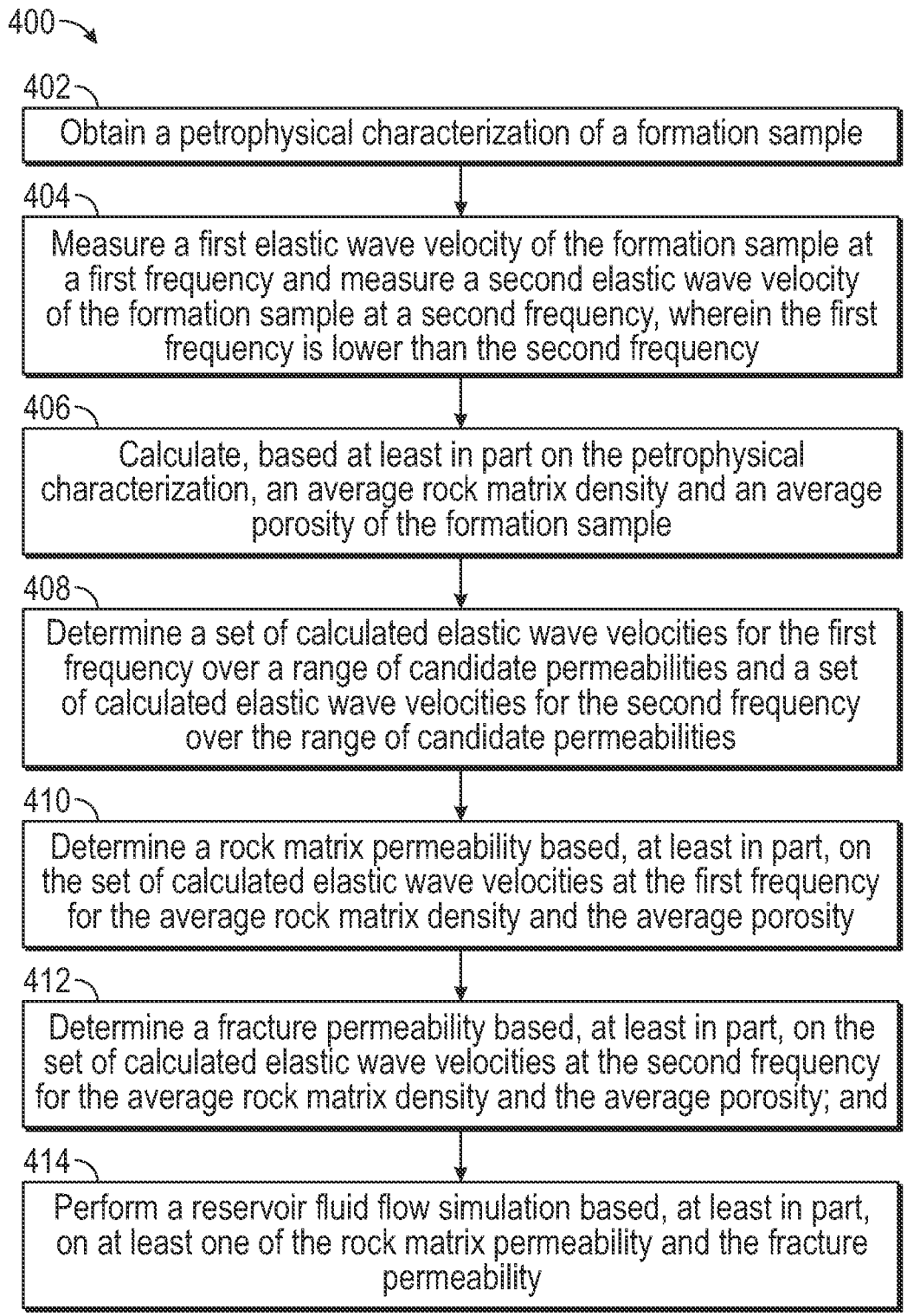
FIG. 4 provides a flowchart in accordance with one or more embodiments.

FIG. 4 provides a flowchart (400) describing a method for determining a rock matrix permeability and a fracture permeability based on a dual porosity dual permeability poroelastodynamic model, in accordance with one or more embodiments disclosed herein. The rock matrix permeability and fracture permeability impact the elastic wave velocity in fluid-saturated rocks.

In Step 402, in accordance with one or more embodiments, a petrophysical characterization of a formation sample may be obtained. The petrophysical characterization may include a variety of properties describing the fractured formation sample. FIG. 5 shows a petrophysical characterization table (500). The petrophysical characterization table (500) is a summary of a subset of parameters (502) with a typical value (504). The parameters shown (502) are only a subset of possible alternative parameters. These alternative parameters may describe addition rock properties such as fluid permeability or may be alternative combinations of the parameters shown (502). For example, Young's modulus and shear modulus may be use as an equivalent alternative to bulk modulus and Poisson's ratio for describing the elastic properties of a sample. The parameters (502) may be obtained by a core sample analyzer or other laboratory equipment or may be derived from measurements therefrom.

In Step 404, a first elastic wave velocity of the formation sample at a first frequency and a second elastic wave velocity of the formation sample at a second frequency may be measured. In accordance with one or more embodiments, the first frequency may be lower than the second frequency. Measuring the elastic wave velocity of a sample may be performed by the core sample analyzer or using other laboratory acoustic equipment or downhole acoustic logging tools.

In Step 406, an average rock matrix density and an average porosity of the formation sample may be calculated. The average rock matrix density and an average porosity of the formation sample may be calculated, based at least in part, on the parameters determined by the petrophysical characterization. The average rock matrix density and average porosity values may vary depending on the type of average used. For example, types of averages that may be employed in Step 406 include but are not limited to an arithmetic average, a geometric average, and a harmonic average. In the dual porosity dual permeability poroelastodynamic model, not all averages yield a unique solution at a selected phase velocity over a range of candidate rock matrix permeabilities or a range of fracture permeabilities.

Figure 6A:
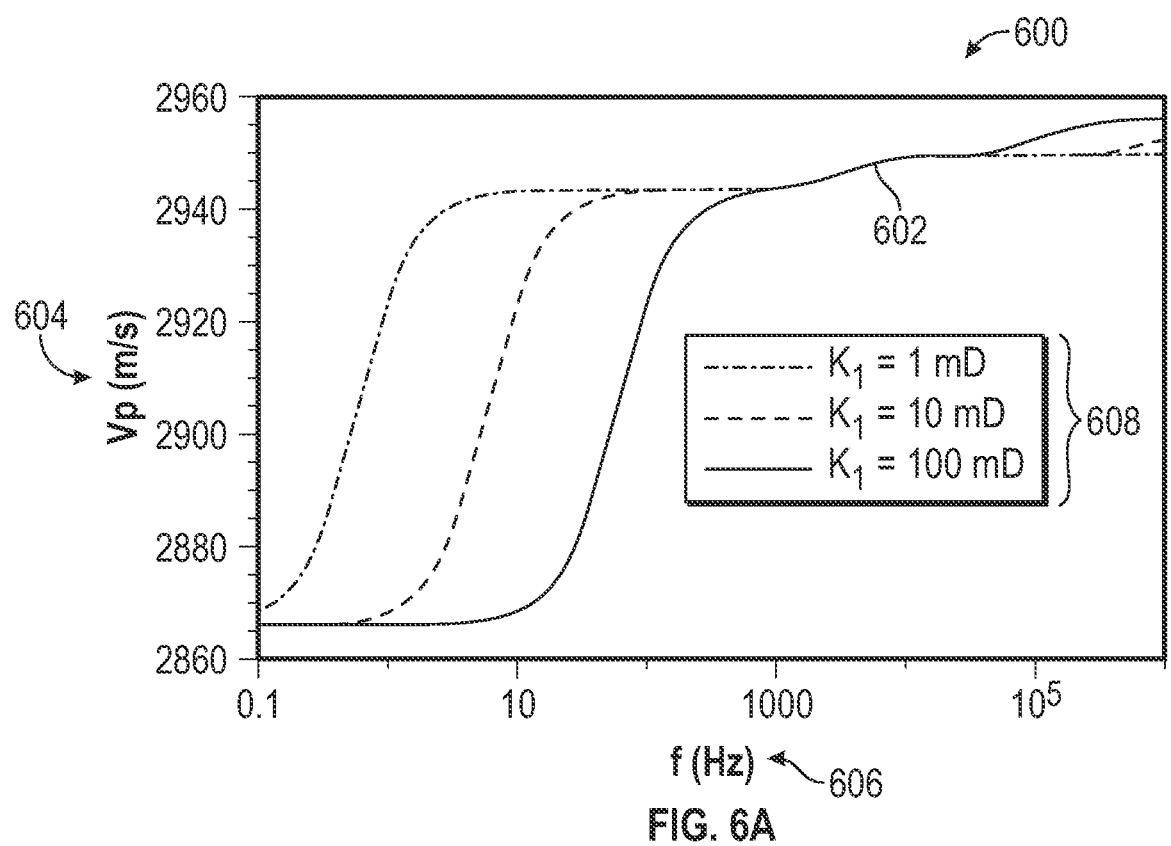
FIG. 6a illustrates an elastic wave velocity spectrum for a plurality of rock matrix permeabilities.
Figure 6B:
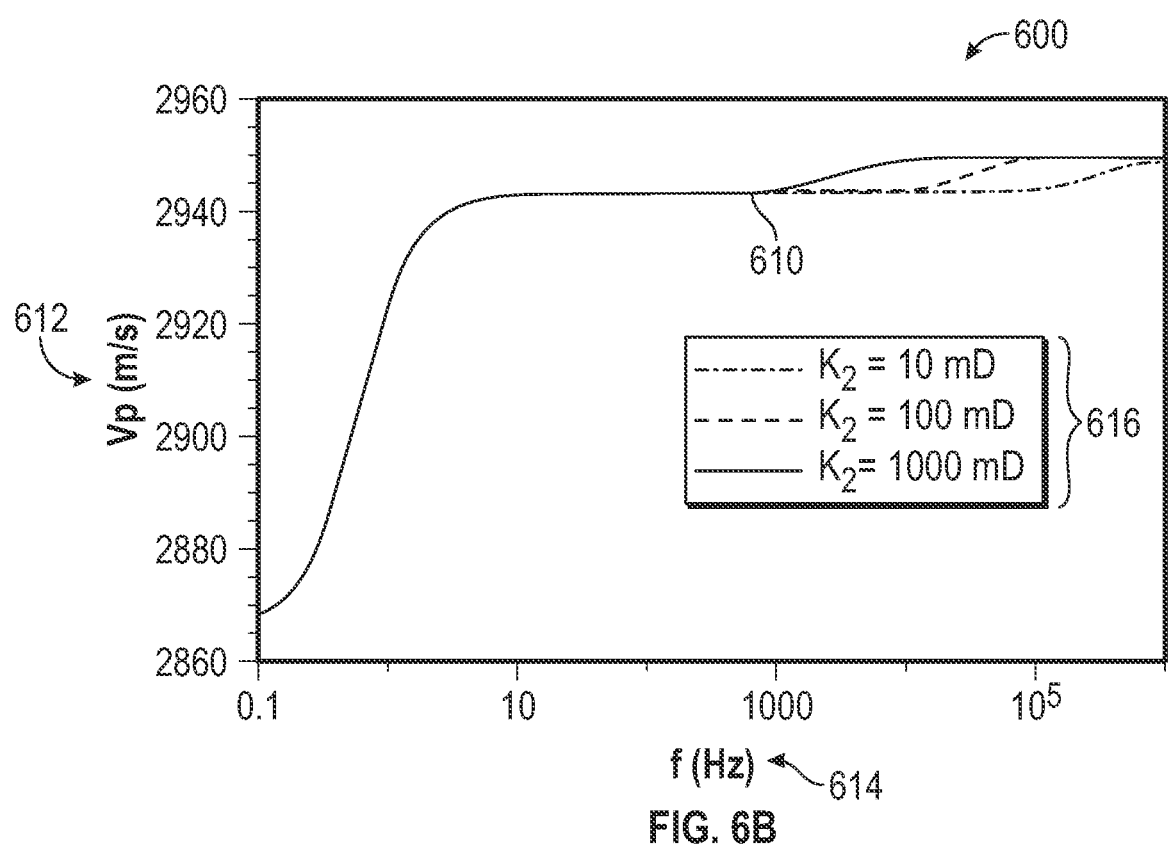
FIG. 6b illustrates an elastic wave velocity spectrum for a plurality of facture permeabilities.

In Step 408 a set elastic wave velocities for the first frequency over a range of candidate permeabilities may be calculated. A set of elastic wave velocities for the second frequency over the range of candidate permeabilities may also be calculated. For example, FIG. 6a and FIG. 6b show a graphical representation of an elastic wave velocity sensitivity analysis (600) to determine the first frequency (FIG. 6a) and at the second frequency (FIG. 6b). FIG. 6a illustrates that the first frequency (602) may be determined through the sensitivity analysis in which the elastic wave velocity (604) varies over a range of frequencies (606) for a range of the rock matrix permeability (608). FIG. 6b illustrates that the second frequency (610) may be determined through a sensitivity analysis in which the elastic wave velocity varies over a range of frequency (614) for a range of the fracture permeability (616). The purpose of the sensitivity analysis may be to identify the first frequency (602) at which the elastic wave velocity may be sensitive to the rock matrix permeability (608) and the second frequency (610) at which the elastic wave velocity (612) may be sensitive to the fracture permeability (616). A frequency below the first frequency can be used to determine the rock matrix permeability. A frequency above the second frequency may be used to determine the fracture permeability.

Figure 7:
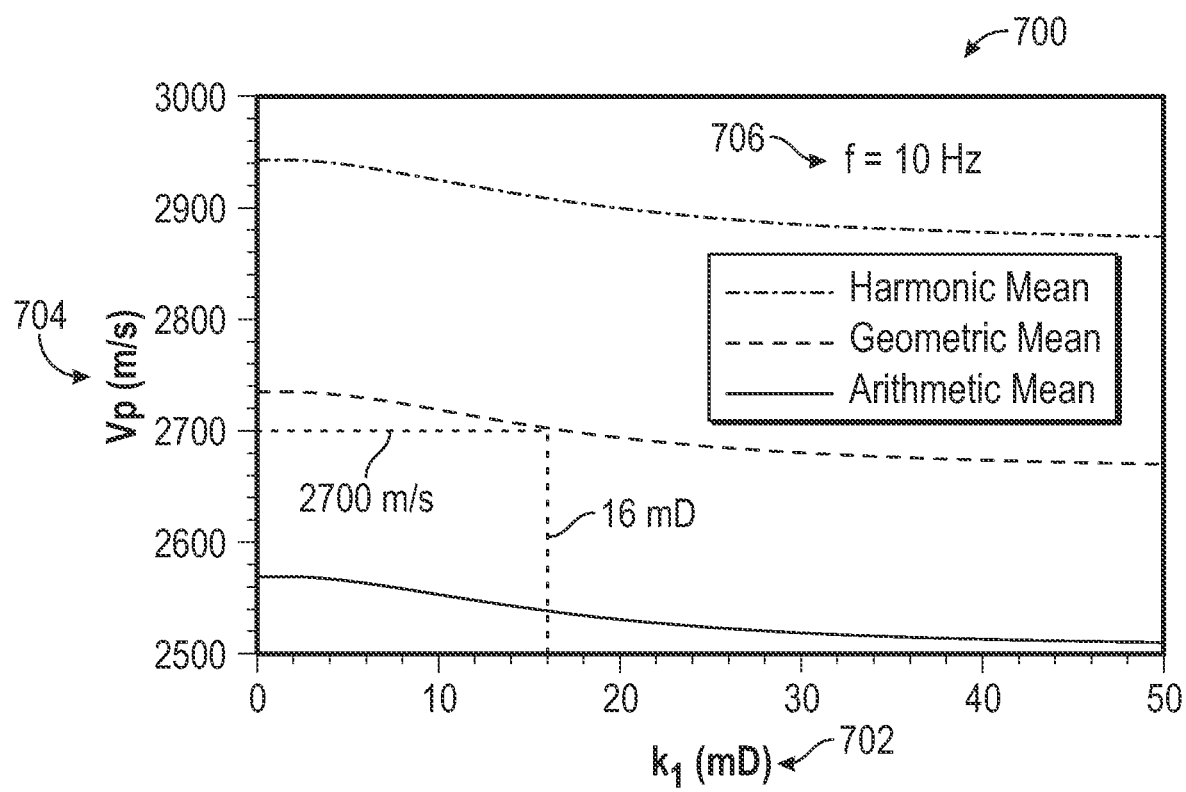
FIG. 7 shows a graphical representation of determining the rock matrix permeability in accordance with one or more embodiments.

Returning now to FIG. 4, in Step 410 a rock matrix permeability based, at least in part, on the set of calculated elastic wave velocities at the first frequency for the average rock matrix density and the average porosity and the measured elastic wave velocity at the first frequency may be determined. FIG. 7 shows an example graphical representation (700) of determining the rock matrix permeability (702) given the first measured elastic wave phase velocity (704) of 2700 m/s at the first frequency (706) of 10 Hz.

Figure 8:
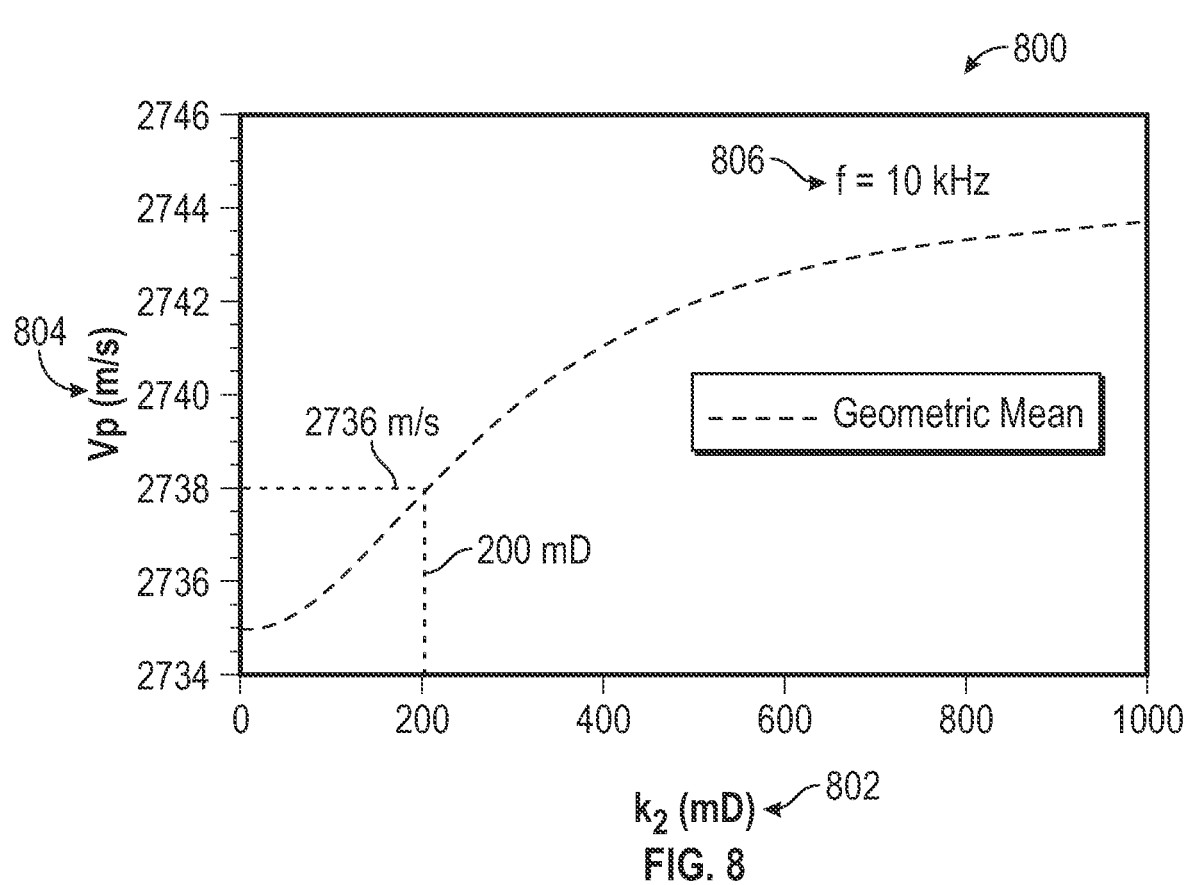
FIG. 8 shows a graphical representation of determining the fracture permeability in accordance with one or more embodiments.

Returning now to FIG. 4, in Step 412 a fracture permeability based, at least in part, on the set of calculated elastic wave velocities at the second frequency for the average rock matrix density and the average porosity and the measured elastic wave velocity at the second frequency may be determined. FIG. 8 shows an example graphical representation (800) of determining the fracture permeability (802) given the second measured elastic wave phase velocity (804) of 2736 m/s at the second frequency (806) of 10 kHz.

Returning now to FIG. 4, in Step 414 a reservoir fluid flow simulation based, at least in part, on at least one of the rock matrix permeability and the fracture permeability may be performed. The results of the reservoir fluid flow simulation may be used to determine a location for a wellbore, which may be used by a drilling system for drilling a wellbore along a wellbore path. In other implementations the reservoir fluid flow simulation may be used, at least in part, for other activities such as making an economic decision, planning a production facility, updating a reservoir model, or optimizing a wellbore location or a wellbore path.

Figure 9:
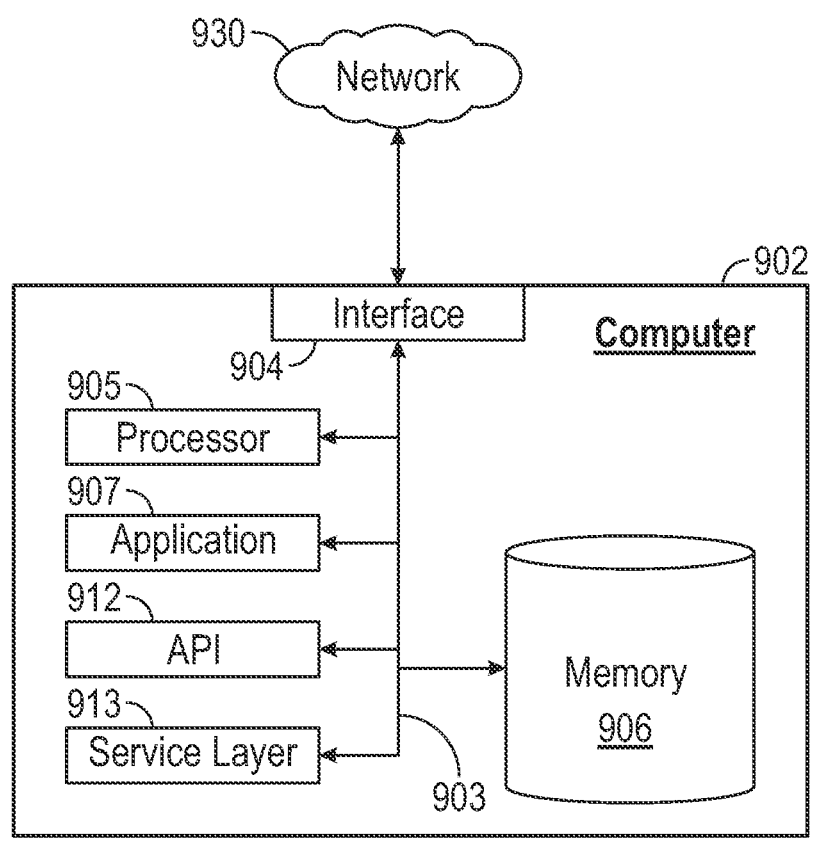
FIG. 9 illustrates a computing device in accordance with one or more embodiments.

FIG. 9 depicts a block diagram of the computer (902) used to provide computational functionalities associated with described algorithms, methods, functions, processes, flows, and procedures as described in this disclosure, according to one or more embodiments. The illustrated computer (902) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (902) may include a computer that includes an input device, such as a keypad, keyboard, touch screen, or other device that can accept user information, and an output device that conveys information associated with the operation of the computer (902), including digital data, visual, or audio information (or a combination of information), or a Graphical User Interface (GUI).

The computer (902) can serve in a role as a client, network component, a server, a database or other persistency, or any other component (or a combination of roles) of a computer system for performing the subject matter described in the instant disclosure. The illustrated computer (902) is communicably coupled with a network (830). In some implementations, one or more components of the computer (902) may be configured to operate within environments, including cloud-computing-based, local, global, or other environment (or a combination of environments).

At a high level, the computer (902) is an electronic computing device operable to receive, transmit, process, store, or manage data and information associated with the described subject matter. According to some implementations, the computer (902) may also include or be communicably coupled with an application server, e-mail server, web server, caching server, streaming data server, business intelligence (BI) server, or other server (or a combination of servers).

The computer (902) can receive requests over network (930) from a client application (for example, executing on another computer (902)) and responding to the received requests by processing the requests in an appropriate software application. In addition, requests may also be sent to the computer (902) from internal users (for example, from a command console or by other appropriate access method), external or third-parties, other automated applications, as well as any other appropriate entities, individuals, systems, or computers.

Each of the components of the computer (902) can communicate using a system bus (903). In some implementations, any or all of the components of the computer (902), both hardware or software (or a combination of hardware and software), may interface with each other or the interface (904) (or a combination of both) over the system bus (903) using an application programming interface (API) (912) or a service layer (913) (or a combination of the API (912) and service layer (913). The API (912) may include specifications for routines, data structures, and object classes. The API (912) may be either computer-language independent or dependent and refer to a complete interface, a single function, or even a set of APIs. The service layer (913) provides software services to the computer (902) or other components (whether or not illustrated) that are communicably coupled to the computer (902). The functionality of the computer (902) may be accessible for all service consumers using this service layer. Software services, such as those provided by the service layer (913), provide reusable, defined business functionalities through a defined interface. For example, the interface may be software written in JAVA, C++, or other suitable language providing data in extensible markup language (XML) format or another suitable format. While illustrated as an integrated component of the computer (902), alternative implementations may illustrate the API (912) or the service layer (913) as stand-alone components in relation to other components of the computer (902) or other components (whether or not illustrated) that are communicably coupled to the computer (902). Moreover, any or all parts of the API (912) or the service layer (913) may be implemented as child or sub-modules of another software module, enterprise application, or hardware module without departing from the scope of this disclosure.

The computer (902) includes an interface (904). Although illustrated as a single interface (904) in FIG. 9, two or more interfaces (904) may be used according to particular needs, desires, or particular implementations of the computer (902). The interface (904) is used by the computer (902) for communicating with other systems in a distributed environment that are connected to the network (930). Generally, the interface (904 includes logic encoded in software or hardware (or a combination of software and hardware) and operable to communicate with the network (930). More specifically, the interface (904) may include software supporting one or more communication protocols associated with communications such that the network (930) or interface's hardware is operable to communicate physical signals within and outside of the illustrated computer (902).

The computer (902) includes at least one computer processor (905). Although illustrated as a single computer processor (905) in FIG. 9, two or more processors may be used according to particular needs, desires, or particular implementations of the computer (902). Generally, the computer processor (905) executes instructions and manipulates data to perform the operations of the computer (902) and any algorithms, methods, functions, processes, flows, and procedures as described in the instant disclosure.

The computer (902) also includes a memory (906) that holds data for the computer (902) or other components (or a combination of both) that can be connected to the network (930). For example, memory (906) can be a database storing data consistent with this disclosure. Although illustrated as a single memory (906) in FIG. 9, two or more memories may be used according to particular needs, desires, or particular implementations of the computer (902) and the described functionality. While memory (906) is illustrated as an integral component of the computer (902), in alternative implementations, memory (906) can be external to the computer (902).

The application (907) is an algorithmic software engine providing functionality according to particular needs, desires, or particular implementations of the computer (902), particularly with respect to functionality described in this disclosure. For example, application (907) can serve as one or more components, modules, applications, etc. Further, although illustrated as a single application (907), the application (907) may be implemented as multiple applications (907) on the computer (902). In addition, although illustrated as integral to the computer (902), in alternative implementations, the application (907) can be external to the computer (902).

There may be any number of computers (902) associated with, or external to, a computer system containing computer (902), wherein each computer (902) communicates over network (930). Further, the term "client," "user," and other appropriate terminology may be used interchangeably as appropriate without departing from the scope of this disclosure. Moreover, this disclosure contemplates that many users may use one computer (902), or that one user may use multiple computers (902).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method comprising:
   obtaining a petrophysical characterization of a formation sample;
   measuring a first elastic wave velocity of the formation sample at a first frequency and measuring a second elastic wave velocity of the formation sample at a second frequency, wherein the first frequency is lower than the second frequency;
   calculating, based on the petrophysical characterization, an average rock matrix density and an average porosity of the formation sample;
   determining a first set of calculated elastic wave velocities at the first frequency over a range of candidate rock matrix permeabilities using the average rock matrix density and the average porosity;
   determining a second set of calculated elastic wave velocities at the second frequency over a range of candidate fracture permeabilities using the average rock matrix density and the average porosity;
   determining a rock matrix permeability based on the first set of calculated elastic wave velocities, the range of candidate rock matrix permeabilities, and the first elastic wave velocity;

determining a fracture permeability based on the second set of calculated elastic wave velocities, the range of candidate fracture permeabilities, and the second elastic wave velocity; and performing a reservoir fluid flow simulation based on at least one of the rock matrix permeability or the fracture permeability;

determining a wellbore path based on the reservoir fluid flow simulation; and drilling, using a drilling system, a wellbore guided by the wellbore path.

2. The method of claim 1, wherein each of the average rock matrix density and the average porosity comprises an arithmetic mean, a geometric mean, or a harmonic mean.

3. The method of claim 1, wherein:
the first elastic wave velocity comprises a measured P-wave phase velocity;
the first set of calculated elastic wave velocities at the first frequency comprises a first set of calculated P-wave phase velocities; and
the second set of calculated elastic wave velocities at the second frequency comprises a second set of calculated P-wave phase velocities.

4. The method of claim 1, further comprising:
obtaining the formation sample from a formation; and
determining at least one petrophysical characteristic among the petrophysical characterization from the formation sample.

5. The method of claim 1, wherein the petrophysical characterization of the formation sample comprises at least one of a density of a mineral grain within the formation sample, a volume fraction of the mineral grain, a density of an organic material within the formation sample, a volume fraction of the organic material, a porosity of the formation sample, or a volume fraction of a fracture within the formation sample.

6. A system comprising:
a core sample analyzer configured to determine:
a petrophysical characterization of a formation sample, and
a first elastic wave velocity at a first frequency and a second elastic wave velocity at a second frequency for the formation sample, wherein the first frequency is lower than the second frequency; and
a computer processor configured to:
receive the petrophysical characterization of the formation sample;
receive the first elastic wave velocity of the formation sample at the first frequency and the second elastic wave velocity of the formation sample at the second frequency, wherein the first frequency is lower than the second frequency;
calculate, based on the petrophysical characterization, an average rock matrix density and an average porosity of the formation sample;
determine a first set of calculated elastic wave velocities at the first frequency over a range of candidate rock matrix permeabilities using the average rock matrix density and the average porosity;
determine a second set of calculated elastic wave velocities at the second frequency over a range of candidate fracture permeabilities using the average rock matrix density and the average porosity;
determine a rock matrix permeability based on the first set of calculated elastic wave velocities, the range of candidate rock matrix permeabilities, and the first elastic wave velocity;

determine a fracture permeability based on the second set of calculated elastic wave velocities, the range of candidate fracture permeabilities, and the second elastic wave velocity;

perform a reservoir fluid flow simulation based on at least one of the rock matrix permeability or the fracture permeability;

determine a wellbore path based on the reservoir fluid flow simulation; and a drilling system configured to drill a wellbore guided by the wellbore path.

7. The system according to claim 6, wherein each of the average rock matrix density and the average porosity comprises an arithmetic mean, a geometric mean, or a harmonic mean.

8. The system according to claim 6, wherein:
the first elastic wave velocity comprises a measured P-wave phase velocity;
the first set of calculated elastic wave velocities at the first frequency comprises a first set of calculated P-wave phase velocities; and
the second set of calculated elastic wave velocities at the second frequency comprises a second set of calculated P-wave phase velocities.

9. The system according to claim 6, wherein the petrophysical characterization of the formation sample comprises at least one of a density of a mineral grain within the formation sample, a volume fraction of the mineral grain, a density of an organic material within the formation sample, a volume fraction of the organic material, a porosity of the formation sample, or a volume fraction of a fracture within the formation sample.

10. A non-transitory computer readable medium storing a set of instructions executable by a computer processor, the set of instructions comprising functionality for:
receiving a petrophysical characterization of a formation sample;
receiving a first elastic wave velocity of the formation sample at a first frequency and a second elastic wave velocity of the formation sample at a second frequency, wherein the first frequency is lower than the second frequency;
calculating, based on the petrophysical characterization, an average rock matrix density and an average porosity of the formation sample;
determining a first set of calculated elastic wave velocities at the first frequency over a range of candidate rock matrix permeabilities using the average rock matrix density and the average porosity;
determining a second set of calculated elastic wave velocities at the second frequency over a range of candidate fracture permeabilities using the average rock matrix density and the average porosity;
determining a rock matrix permeability based on the first set of calculated elastic wave velocities, the range of candidate rock matrix permeabilities, and the first elastic wave velocity;
determining a fracture permeability based on the second set of calculated elastic wave velocities, the range of candidate fracture permeabilities, and the second elastic wave velocity;
performing a reservoir fluid flow simulation based on at least one of the rock matrix permeability or the fracture permeability;
determining a wellbore path based on the reservoir fluid flow simulation, wherein a wellbore guided by the wellbore path is drilled by a drilling system.

11. The non-transitory computer readable medium of claim 10, wherein:
- the first elastic wave velocity comprises a measured P-wave phase velocity;
- the first set of calculated elastic wave velocities at the first frequency comprises a first set of calculated P-wave phase velocities; and
- the second set of calculated elastic wave velocities at the second frequency comprises a second set of calculated P-wave phase velocities.

12. The non-transitory computer readable medium according to claim 10, wherein the petrophysical characterization of the formation sample comprises at least one of a density of a mineral grain within the formation sample, a volume fraction of the mineral grain, a density of an organic material within the formation sample, a volume fraction of the organic material, a porosity of the formation sample, or a volume fraction of a fracture within the formation sample.

* * * * *